United States Patent
Yost et al.

(10) Patent No.: US 6,475,147 B1
(45) Date of Patent: Nov. 5, 2002

(54) ULTRASONIC APPARATUS AND TECHNIQUE TO MEASURE CHANGES IN INTRACRANIAL PRESSURE

(75) Inventors: William T. Yost, Newport News; John H. Cantrell, Williamsburg, both of VA (US)

(73) Assignee: The United States of America as represented by the United States National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/493,044

(22) Filed: Jan. 27, 2000

Related U.S. Application Data

(60) Provisional application No. 60/117,378, filed on Jan. 27, 1999.

(51) Int. Cl.[7] .................................................. A61B 8/00
(52) U.S. Cl. ...................................... 600/438; 600/451
(58) Field of Search ................................ 600/437–472, 600/561, 485, 454, 559; 73/24.05

(56) References Cited

U.S. PATENT DOCUMENTS

| | | |
|---|---|---|
| 4,703,758 A | 11/1987 | Omura |
| 4,971,061 A | 11/1990 | Kageyama et al. |
| 5,214,955 A * | 6/1993 | Yost et al. ................ 73/24.05 |
| 5,388,583 A * | 2/1995 | Ragauskas et al. ......... 600/451 |
| 5,617,873 A * | 4/1997 | Yost et al. .................. 600/561 |

OTHER PUBLICATIONS

Yost et al., Fundamental Aspect of Pulse Phase–locked Loop Technology–based Methods for Measurement of Ultrasonic Velocity. J. Acoustic Soc. Am. 91, 1456–1468, (1992).*

* cited by examiner

Primary Examiner—Marvin M. Lateef
Assistant Examiner—Riley Jain
(74) Attorney, Agent, or Firm—Helen M. Galus

(57) ABSTRACT

Changes in intracranial pressure can be measured dynamically and non-invasively by monitoring one or more cerebrospinal fluid pulsatile components. Pulsatile components such as systolic and diastolic blood pressures are partially transferred to the cerebrospinal fluid by way of blood vessels contained in the surrounding brain tissue and membrane. As intracranial pressure varies these cerebrospinal fluid pulsatile components also vary. Thus, intracranial pressure can be dynamically measured. Furthermore, use of acoustics allows the measurement to be completely non-invasive. In the preferred embodiment, phase comparison of a reflected acoustic signal to a reference signal using a constant frequency pulsed phase-locked-loop ultrasonic device allows the pulsatile components to be monitored. Calibrating the device by inducing a known change in intracranial pressure allows conversion to changes in intracranial pressure.

11 Claims, 5 Drawing Sheets

ULTRASONIC APPARATUS AND TECHNIQUE TO MEASURE CHANGES IN INTRACRANIAL PRESSURE

CLAIM OF BENEFIT OF PROVISIONAL APPLICATION

Pursuant to 35 U.S.C. §119, the benefit of priority from provisional application 60/117,378, with a filing date of Jan. 27, 1999, is claimed for this non-provisional application.

ORIGIN OF THE INVENTION

The invention described herein was made in the performance of work done by employees of the United States Government and may be manufactured and used by or for the government for governmental purposes without the payment of any royalties thereon or therefore.

TECHNICAL FIELD

This invention relates generally to measuring intracranial pressure in patients, and more particularly to measuring intracranial pressure by non-invasively monitoring the pulsatile components of cerebrospinal fluid contained within the head.

BACKGROUND

Intracranial pressure (ICP) is an important parameter in the management of closed head trauma. For example, head trauma can cause edema which leads to increased ICP as well as decreased brain compliance. High ICP must therefore be treated aggressively in order to prevent secondary neurological damage. Conditions, other than trauma, which can lead to elevated ICP include intracerebral hematoma, central nervous system infections, subarachnoid hemorrhage, space-occupying lesions, increased gravitational forces and whole body acceleration. When ICP is elevated, it can vary widely from moment to moment and dynamic measurement of ICP is extremely useful. Dynamic measurement of ICP may also provide evidence of hypertension before the onset of clinical signs and symptoms.

Most current methods for measuring ICP are invasive, either utilizing an intraventricular catheter, a subarachnoid screw, an epidural pressure sensor or a sound wave burst into the inner ear. The leading complications of invasive ICP monitoring are insertion-related hemorrhage and hematoma formation, acute overdrainage of cerebrospinal fluid, and infection. An example of the generation of a sound wave causing the bones of the middle ear to react and transfer pressure to the eardrum can be found in U.S. Pat. No. 4,841,986 issued to Marchbanks. In addition to the extreme discomfort to the patient resulting from such a method, the results are not very accurate.

Although other methods claim to non-invasively measure ICP, they either measure some physiological quantity that has no fixed relationship to ICP or the relationship only allows for static ICP measurements accompanied by fairly complex calibration schemes. A method described by U.S. Pat. No. 5,617,873 issued to Yost and Cantrell, describes the non-invasive use of a constant frequency pulsed phase-locked-loop (CFPPLL) ultrasonic device to statically measure ICP. While such an ultrasonic technique is painless and effective in reducing the invasiveness of the ICP measurement, other problems are left unsolved. The CFPPLL receives a reflected toneburst signal from the front of the head and phase compares the reflected signal to a reference signal. The difference in phase between the two signals is attributed to changes in cerebrospinal fluid volume which is due to ICP changes. The phase comparison results in a control voltage which represents the amount of voltage required to bring the two signals into quadrature. A pressure-volume index along with a fairly complex calibration scheme utilizing either a tiltable bed or pressurized cap allows for the conversion from control voltage to cerebrospinal fluid volume, to ICP. The limitation associated with such a method, is that the ICP measurements are relatively static because they depend on changes in the cerebrospinal fluid volume, a relatively static physiological quantity. Furthermore, the device as described lacked sufficient responsiveness to measure dynamic quantities. The calibration scheme is also sufficiently complex to limit the clinical usefulness of the method.

STATEMENT OF INVENTION

Accordingly, one object of the invention is to non-invasively measure ICP within a patient's head.

A further object of the invention is to measure ICP by using a non-invasive ultrasonic measurement device.

A further object of the invention is to monitor physiological quantities such as pulsatile components which enable accurate, dynamic ICP measurements to be made.

Another object is to use a measurement device with sufficient responsiveness to monitor dynamic quantities.

Still another object is to allow measurement of ICP with a relatively simple calibration scheme.

Additional objects and advantages of the present invention are apparent from the drawings and specification which follow.

SUMMARY OF THE INVENTION

The present invention monitors one or more blood pressure pulsatile components present in the brain as a method of measuring ICP. Examples of these pulsatile components are systolic and diastolic blood pressures which are partially transferred to the cerebrospinal fluid (CSF) contained in the head. Overall blood pressure is maintained by the complex interaction of the homeostatic mechanisms of the body and is moderated by the volume of the blood, the lumen of the arteries and arterioles, and the force of the cardiac contractions. These cardiac contractions transfer arterial pulses to the blood vessels in the brain tissue and the membrane surrounding the CSF. The blood vessels in turn partially transfer the arterial pulses to the adjacent CSF. Continuous monitoring of these pulses allows ICP measuring because as the ICP varies, the pulsatile components of the CSF also vary. Capitalizing on this direct relationship for the purpose of non-invasively measuring ICP is not found in the prior art.

The present invention generates an acoustic signal on one side of the head which is reflected back from the other side of the head. As the reflected acoustic signal travels through the brain, pulsatile variations in the CSF cause associated phase variations in the signal. The preferred embodiment of the present invention utilizes the phase shifting capabilities of the CFPPLL described by U.S. Pat. No. 5,214,955 issued to Yost and Cantrell to monitor this variation in the CSF pulsatile components, which patent is herein incorporated by reference, as if set forth in its entirety. After receiving the phase varied acoustic signal and converting it into a phase varied electrical signal, the CFPPLL phase compares the electrical signal to a reference signal, generates an error signal in relation to the difference in phase between the two signals, integrates the error signal into a control voltage, and shifts the phase of the reference signal based on the control voltage such that the two signals are placed in quadrature.

By integrating the error signal into a measurement voltage with filtering circuitry having appropriate responsiveness to biological systems, a signal can therefore be sampled and compared frequently enough to dynamically monitor pulsatile components. Such circuitry simply requires the appropriate time constant and is commonly known in the field. The present invention also employs a relatively simple calibration method to convert the pulsatile components into ICP with a measurement baseline. The method involves tilting the head to a new position to cause a change in ICP of a known amount. The tilt also causes a change in the CSF pulsatile components, which causes a change in the error signal and associated measurement voltage. The change in known ICP divided by the associated change in measurement voltage allows a measurement baseline to be obtained and therefore permits monitoring of the pulsatile components associated with subsequent changes in ICP. Since respiration pulses also affect intracranial pressure, a system which monitors blood gases can be used as an alternative calibration method should tilting the head be deemed undesirable.

Further, another possible calibration method to account for changes in the pulsatile components caused by changes in blood pressure could be achieved by correlating the change in measurement voltage with changes in blood pressure measured at a different point on the body, such as the wrist.

BRIEF DESCRIPTION OF THE DRAWINGS

A more complete appreciation of the invention and the many of the attendant advantages thereof will be readily obtained as the same becomes better understood by reference to the following detailed description when considered in connection with accompanying drawings, wherein:

FIG. 4 and FIG. 5 depict examples of two Pulsed Phase-Locked Loop (PPLL) mechanisms each of which could be used in accordance worth a least on embodiment of the present invention. Central to the operation of both constant frequency and variable frequency pulse phase-locked instrument is the output of a phase detector that phase compares the signal from the sample to a reference signal. A selected portion of the signal from the sample is fed through an integrator circuit to a control loop that alerts the signals to the phase detector until its output is nulled. At that point, the system stabilizes and the appropriate instrument output is recorded.

Figure 4:
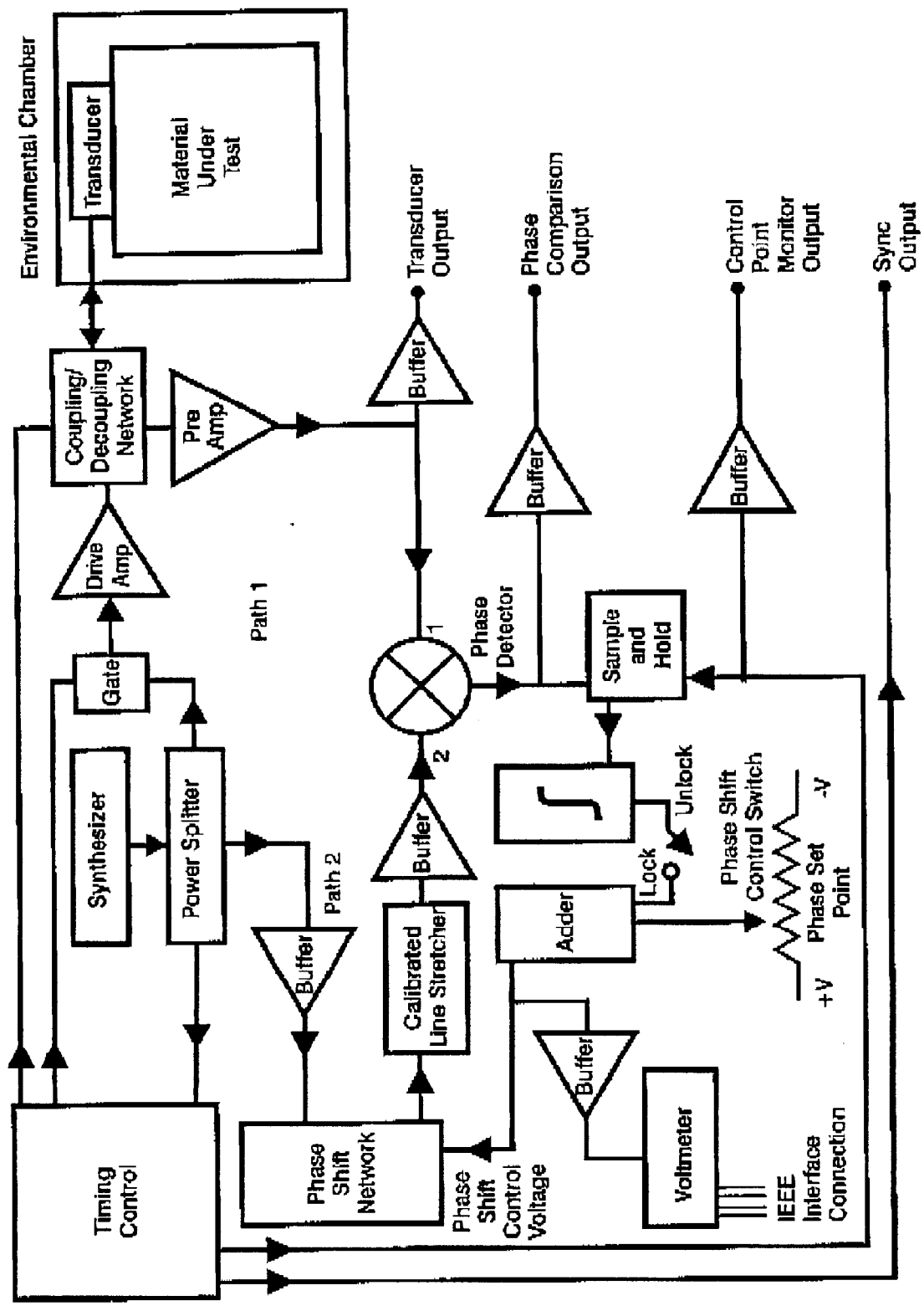
FIG. 4 is a block diagram of a constant frequency phase-locked loop (CFPPLL) instrument.

(A) The constant frequency pulse phase-locked loop (FIG. 4)

An understanding of the basic operation of the CFPPLL system can be obtained by considering a constant frequency oscillator and two signal paths. Along the first path (the measurement path), the acoustic signal is generated and, after traversal of the acoustic medium and electro-conversion by the transducer is amplified. The second path, which includes a voltage-controlled phase shifter (VCPS), is the reference path used for phase comparison with the first path. The phase detector detects the relative phase difference between the two paths with an output voltage that is proportional to the cosine of the phase difference. The control voltage to the VCPS is automatically changed until the output of the detector is 0 V, a condition of quadrature between the signals. A calibration procedure that uses a line stretcher in the reference path permits the conversion of the change voltage to a change in phase shift between the two paths.

With the above basic principles of operation in mind, we consider the block of the instrument shown in FIG. 4. We begin with a frequency synthesizer and a power splitter. In addition to path 1 (measurement path) and path 2 (reference path), the power splitter feeds timing circuits, which generates all timing pulses. Path 1 shows the progression from the frequency synthesizer source to the gate where an adjustable width toneburst is formed. The toneburst is power boosted by the drive amplifier and couple to the transducer through the coupling-decoupling to form an acoustic toneburst. To minimize preamplifier overload, it is decoupled form the large voltage output of the drive amplifier. The acoustic toneburst travels through the acoustic propagation medium (sample), is reflected at the end of the path, traverse the medium in the opposite direction, and impinges upon the transducer as an echo from the original pulse (pulse echo). Any change in the propagation medium (e.g., velocity changes or path length changes) produces an associated phase change in path 1.

After electrical conversion by the transducer, the echo signal is routed to the preamplifier by the coupling-decoupling network that isolates the signal form the low-impedance path presented by the output impedance of the drive amplifier. The preamplifier boosts the signal voltage that is then sent to one input of the phase detector. The preamplifier output is also buffed and made available for monitoring by an oscilloscope.

Path 2 is the reference signal path from the frequency synthesizer to the phase detector. The input to the VCPS network is routed form a buffer that provides a match for the electrical input impedance of the phase shift network. The phase shift is controlled by a devoltage applied to the control pin of the VCPS. The output of the VCPS passes through a line stretcher for calibration of the system, and then to a buffer to the phase detector. During data collection, no adjustment to the line stretcher is made.

Phase comparison of the two paths is performed by the phase detector, which is a product in series with a low-pass filter. The phase detector output voltage is equal to one-half the product of the input voltage amplifies times the cosine of the phase differences between the two signals. The output is passed to the sample and hold circuit, which selects the desired portion of the phase signal, and to an output port through a buffer for observation with an oscilloscope. The portion of the phase signal chosen for measurement is selected by an adjustable timing pulse to the sample and hold circuit whose output is sent to the intergrator. The integrator is part of the loop control circuit.

The loop control circuit, which is made up of the sample and hold, the integrator, the phase set point potentiometer, and the adder provides the control voltage for the phase shift network. The control voltage is the sum of the integrator output and the phase set point potentiometer voltages. The phase set point potentiometer sets the nominal phase shift about which the system operates while the integrator provides a voltage derived from the phase detector. When the phase detector output reaches null, the integrator output voltage stabilizes to a constant value and quadrature between paths 1 and 2 is established. The phase shift control switch is normal in the "locked" 0 state when the system is taking a measurement. For set-up, it is moved to the "unlocked" state so that the phase shift is under manual control through the phase set point potentiometer.

The timing control section controls the timing sequences and forms all necessary timing signal used in the circuit. Timing signals are referenced to the repetition rate that is determined by counting down from the frequency synthesizer. The sync output marks the beginning of the formation of the toneburst and is used for measurement set-up and display. An adjustable width of the toneburst and is also provided. Signals to the coupling-decoupling network and the sample and hold circuit are controlled by the potentiometer and switch settings in this section (not shown on the diagram). Timing sequences are adjusted with the aid of an oscilloscope.

Adjustments for measurements are made with the outputs properly connected to the oscilloscope and the phase shift control switch in the "unlocked" position. The received tonebursts and the phase comparison output voltage are displayed. The frequency of the synthesizer is adjusted so that the amplitudes of the reflected toneburst are far out of the noise and the phase comparison output voltage is relatively "flat topped" for the toneburst reflection (echo) chosen for measurement. An adjustment of the drive amplitude is made if additional signal amplitude is needed. The set point potentiometer is adjusted until the phase comparison voltage corresponding to the desired toneburst reaches approximately 0 V, The control point is adjusted so that the phase signal is sample in its latter half. Because of a time delay in the filter following the phase detector, the phase signal is not precisely synchronized with the tonebursts. The phase shift control switch is placed in the "locked" position for data taking.

Calibration of the VCPS network is accomplished while keeping the system locked onto the point used during the measurement. After recording the voltmeter reading and with the phase shift control switch in the locked position, the calibrated electrical line stretcher is adjusted for a measured phase shift in path 2. After the system stabilizes, the voltmeter reading is recorded. The change in phase shift control voltage is calculated and the change of output voltage for a corresponding phase shift is thus determined. This method is used to calculate small changes to the measured phase shifts, which is particularly important in set-ups requiring the measurement of small phase shifts (of the order of several hundred microradians).

B. The variable frequency pulse phase-locked loop (FIG. 5)

Figure 5:
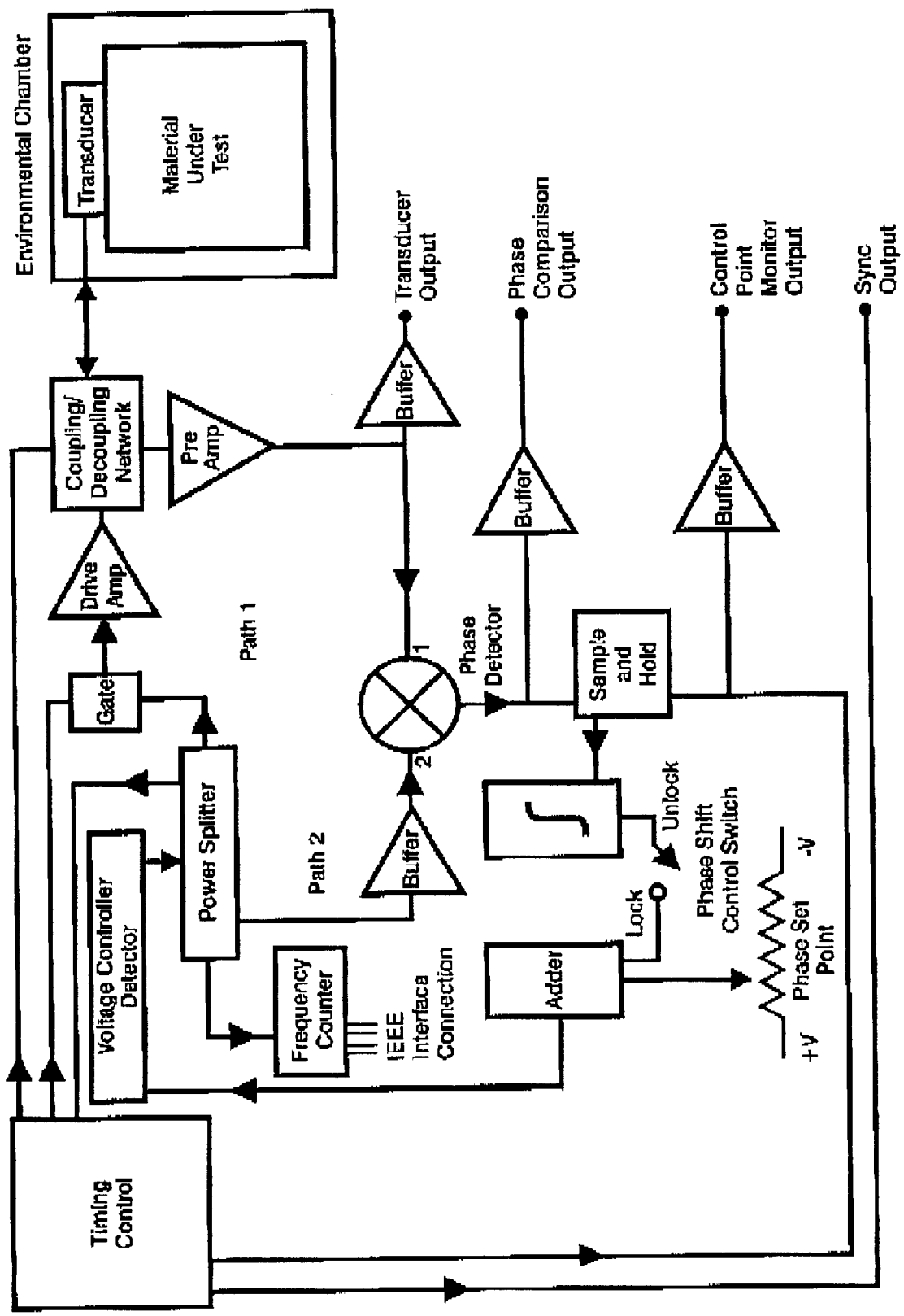
FIG. 5 is a block diagram of a variable frequency phase-locked loop (VFPPLL) instrument.

A block diagram of the VFPPLL is shown in FIG. 5. The frequency of the voltage control oscillator (VCO) is change by the loop control circuit until quadrature between the two paths is obtained. With the exception of the constant frequency source and the phase shift circuity the elements of the CFPPLL are identical with the VFPPLL. The similarities are evident upon comparing FIGS. 4 and 5.

DETAILED DESCRIPTION OF THE INVENTION

Figure 1:
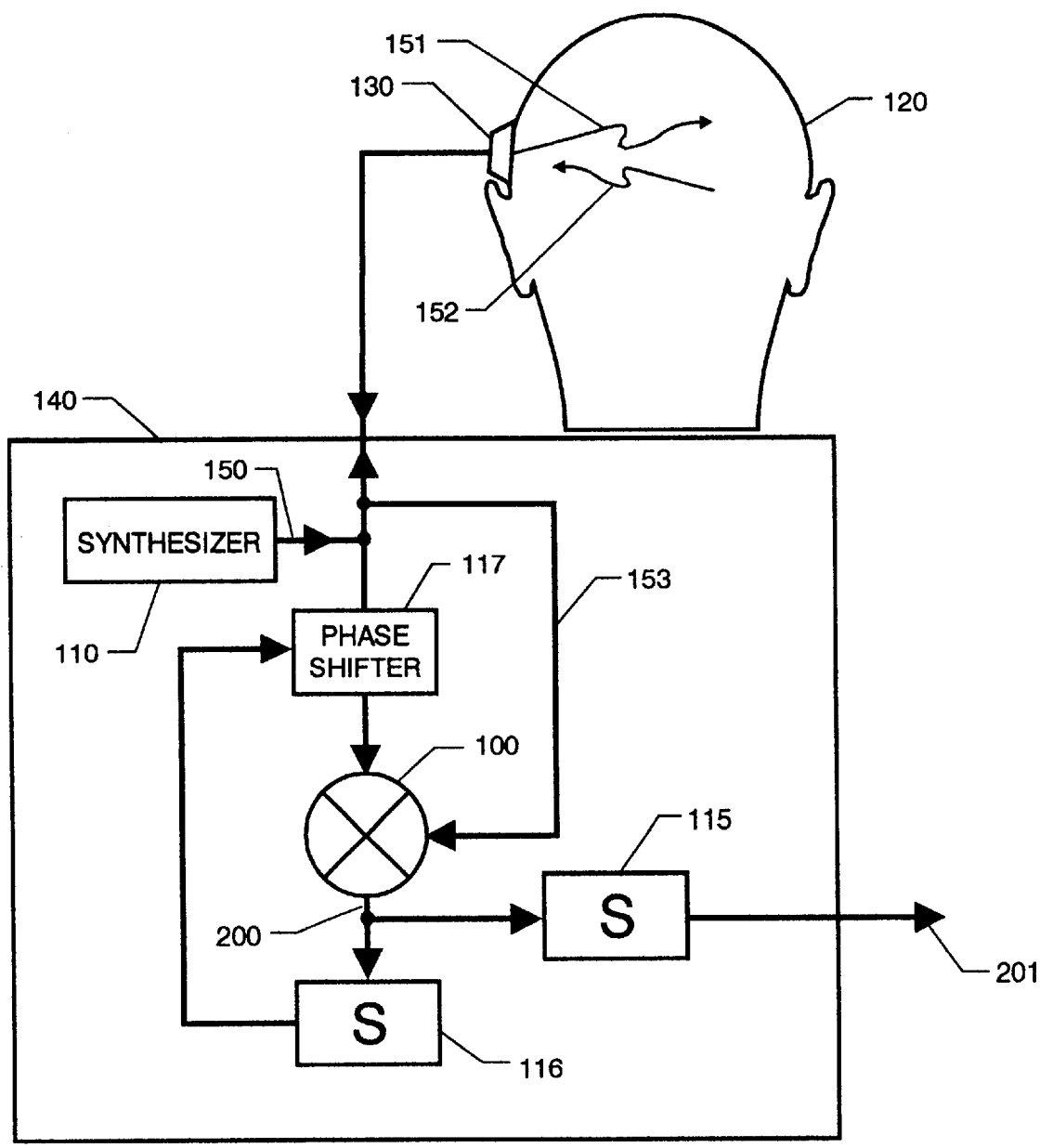
FIG. 1 is a simplified schematic diagram of the preferred measurement device.

The present invention employs a pulsed phase-locked-loop (PPLL), which can be in the form of a constant frequency PPLL (CFPPLL) or a variable frequency PPLL (VFPPLL). FIG. 1 illustrates a simplified schematic diagram of essential components of the preferred embodiment for the non-invasive intracranial pressure monitoring system. As shown in FIG. 1 the present invention can preferably employ a CFPPLL measurement device 140 having a synthesizer 110 for generating an electrical reference signal 150, and a transducer 130 for converting it into an acoustic reference signal 151. The transducer 130 transmits the acoustic reference signal 151 into the patient head 120 and it is reflected back to the transducer 130 in the form of a phase varied acoustic signal 152. The transducer 130 then converts the phase varied acoustic signal 152 into a phase varied electrical signal 153. Use of acoustics enables the method to be completely non-invasive. The phase variation in the acoustic signal 152 is a function of pulsatile variations in the CSF contained in the patient head 120. A phase detector 100 compares the phase of the electrical reference signal 150 and phase varied electrical signal 153. The output of the phase detector 100 is an error signal 200 which is proportional to the difference in phase from quadrature. The amount of voltage required to shift the phase of the electrical reference signal 150 to quadrature with the phase varied electrical signal 153 is obtained by the electrical integration of error signal 200 using integrator 116. Integrator 116 has a sufficient time constant to allow dynamic sampling and comparison of signals. A phase shifter 117 can be provided to perform the phase shift of the electrical reference signal 150 to quadrature with the phase varied electrical signal 153. Filtering circuitry 115 is responsive to biological systems and the result is a measurement voltage 201 that responds to the different timing requirements of the intracranial complex. That is to say, that in at least one embodiment the filtering circuitry 115 can be chosen to correspond to a particular biological system, e.g., pulse rate, respiration rate, etc.

Figure 2A:
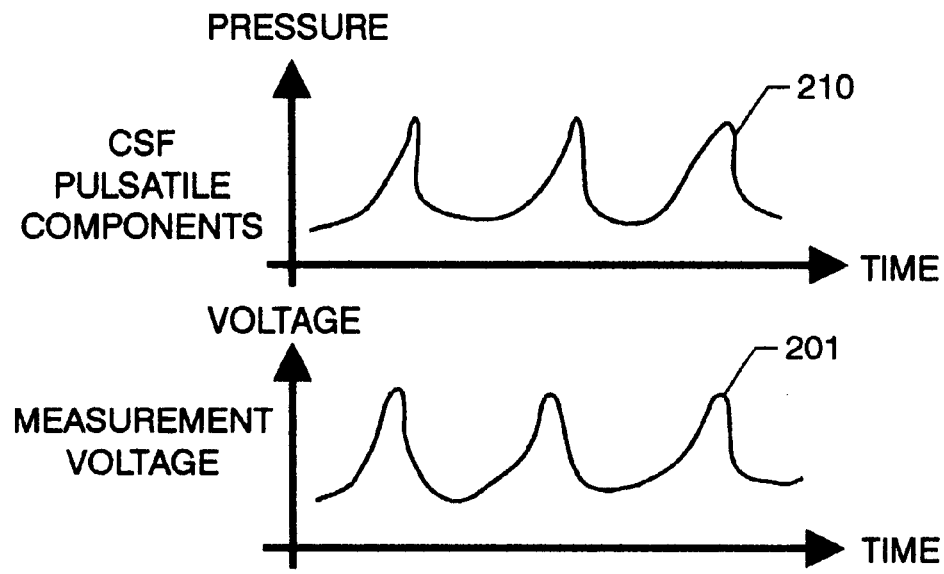
FIG. 2A is a graphical representation of CSF pulsatile components in relation to measurement voltage.
Figure 2B:
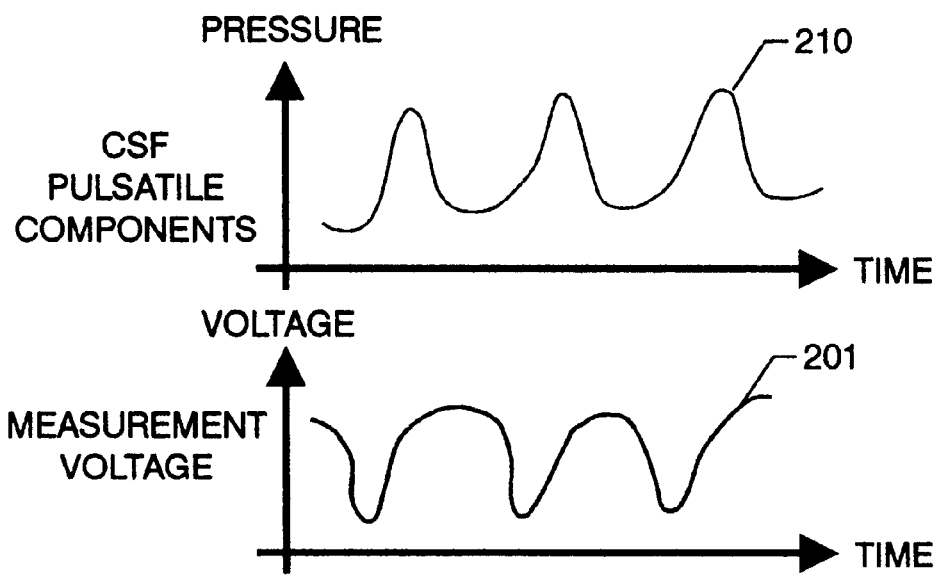
FIG. 2B is another graphical representation of CSF pulsatile components in relation to measurement voltage.

FIG. 2A illustrates the relationship between the CSF pulsatile components 210 present in the patient head 120 and the measurement voltage 201 whose origin is taken from the phase detector 100. The measurement device 140 can be calibrated by tilting the patient head 120 such that a known change in ICP is induced. The tilt also induces a change in the CSF pulsatile components 210, which is sensed by the corresponding skull expansion, and an associated measurement voltage 201. By measuring the voltage 201, the CSF pulsatile components 210 can be inferred. By dividing the known change in ICP by the change in the measured control voltage 201, a measurement baseline is obtained. The changes in the pulsatile components can therefore be dynamically converted into changes in ICP with the measurement baseline. FIG. 2B merely shows an inverted signal, as compared to FIG. 2A, which could result from an opposite polarity of the output voltage.

While the preferred embodiment employs a transducer 130 to transmit and receive the ultrasonic (acoustic) signals, any means for receiving an acoustic signal from the patient's head will suffice. Also, measurement devices other than a CFPPLL can be used as means for determining the pulsatile component of the acoustic signal, and associated ICP. In other possible embodiments of the present invention other known phase shifting capabilities of PPLLs can be utilized to monitor this variation in the CSF pulsatile components, for example, as explained in the article by Yost, et al., *Fundamental Aspects of Pulse Phase-locked Loop Technology-based Methods for Measurement of Ultrasonic Velocity,* J. Acoust. Soc. Am. 91, 1456–1468 (1992), which article is incorporated herein by reference.

Figure 3:
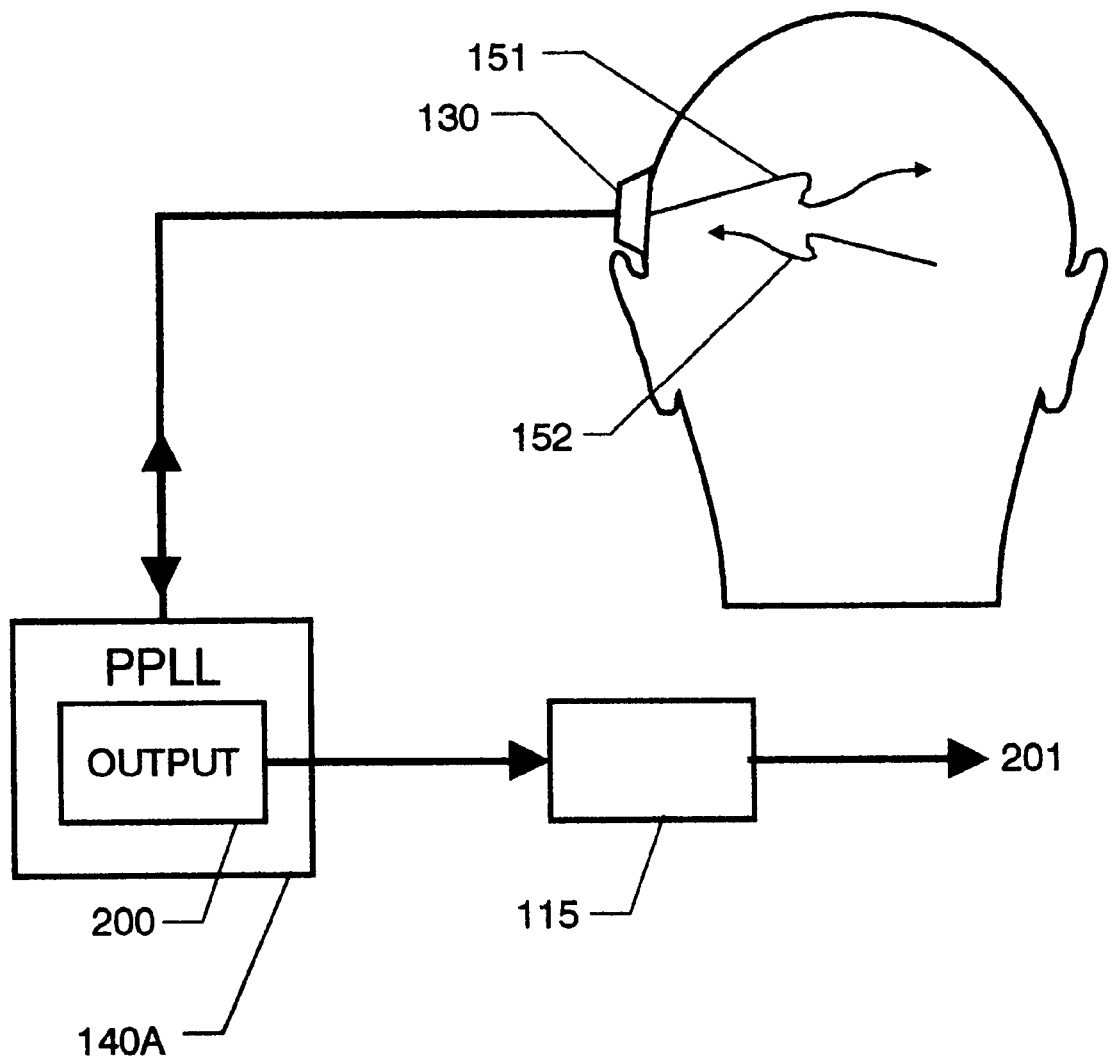
FIG. 3 is a simplified schematic diagram of a preferred measurement device.

FIG. 3 illustrates a simplified schematic diagram of some of the essential components of a preferred embodiment for the non-invasive intracranial pressure monitoring system. FIG. 3 shows a PPLL measurement device 140A which can be in the form of a CFPPLL or a VFPPLL. As explained in more detail above, a transducer 130 can be placed on the side of a person's head as shown in FIG. 3. In at least one embodiment, this transducer can have a resonant frequency of less than about 1 megahertz, and generates an ultrasonic signal of about 500 kilohertz. The head can be tilted from one position to a new position. This tilting causes a change in ICP of a known amount. It also causes a change in error signal output 200 (for example, the sample and hold output 200 from the phase detector signal) which can go to the integrator and then to the phase shifter, as explained above. As a tilt causes a change in output voltage, it also causes a corresponding change in ICP. The change in ICP divided by the change in voltage permits the determination of the pulsatile components in the phase shifter output, thus the dynamic changes in ICP can be determined. Filtering circuitry 115 can be responsive to biological systems and the result is a measurement voltage 201 that responds to the different timing requirements of the intracranial complex.

In constant frequency systems all of the functions can also be performed with digital electronics. As an example, rather than detecting the phase differences. between the echo signal and reference signal, and using the integrated phase difference to drive the signals to quadrature, the echo signal and the reference signal can be digitally recorded, and the phase difference determined by use of computer algorithms. As further example, timing control, gating, waveform generation (synthesizer), coupling/decoupling function, and even the preamp function, can be performed by digital electronics or an appropriately programmed digital computer.

Various methods may be used to calibrate the present inventive device by providing known changes in ICP, as for example disclosed in U.S. Pat. No. 5,617,873 issued to Yost et al. at column 5, line 32 thru column 6, line 14, which is incorporated herein by reference.

It should be understood by those skilled in the art that the descriptions and illustrations herein are by way of examples and the invention is not limited to the exact details shown and described. For example, it should be understood that any device that produces a controlled phase shift in response to a control signal may be used; for example, a current controlled phase shifter or an optically controlled phase shifter. Further, for example, any means of phase detection may be used, for example, a synchronous detector, a homodyne detector, an analog mixer, or a digital mixer.

What is claimed is:

1. A method for non-invasive measurement of changes in intracranial pressure in a patient's head comprising the steps of:
   receiving an acoustic signal from the patient's head;
   determining a pulsatile component of the acoustic signal; and
   determining a change in total intracranial pressure from changes in the pulsatile component.

2. The method for non-invasive measurement of changes in intracranial pressure of claim 1 wherein the step of determining a pulsatile component of the acoustic signal comprises:
   determining a difference in phase between the acoustic signal and a reference signal;
   generating a measurement voltage based on the difference in phase;
   and
   monitoring the measurement voltage such that the pulsatile component of the acoustic signal can be determined.

3. The method for non-invasive measurement of changes in intracranial pressure of claim 2 wherein the step of determining intracranial pressure from the pulsatile component comprises:
   calibrating a measurement device by inducing a known change in intracranial pressure and measuring the change in the measurement voltage;
   dividing the known change in intracranial pressure by the change in the measurement voltage to obtain a measurement baseline; and
   converting the change in pulsatile component into a change in intracranial pressure with the measurement baseline.

4. The method for non-invasive measurement of changes in intracranial pressure of claim 1 wherein the pulsatile component represents systolic blood pressure partially transferred to the cerebrospinal fluid.

5. The method for non-invasive measurement of changes in intracranial pressure of claim 1 wherein the pulsatile component represents diastolic blood pressure partially transferred to the cerebrospinal fluid.

6. An apparatus for non-invasive measurement of changes in intracranial pressure in a patient's head comprising:
   means for receiving an acoustic signal from the patient's head;
   means for determining a pulsatile component of the acoustic signal; and
   means for determining changes in total intracranial pressure from changes in the pulsatile component.

7. The apparatus for non-invasive measurement of changes in intracranial pressure in a patient of claim 6 wherein the means for determining a pulsatile component of the acoustic further comprises:
   filtering circuity with a frequency response capable of dynamically monitoring the pulsatile component; and
   a constant frequency pulse phase-locked loop measurement device.

8. The apparatus for non-invasive measurement of changes in intracranial pressure in a patient of claim 6 wherein the means for determining a pulsatile component of the acoustic signal further comprises:
   filtering circuity with a frequency response capable of dynamically monitoring the pulsatile component; and
   a variable frequency pulse phase-locked loop measurement device.

9. A method for non-invasive measurement of changes in intracranial pressure in a patient's head comprising the steps of:
   receiving an acoustic signal from the patient's head;
   determining a pulsatile component of the acoustic signal;
   determining a change in intracranial pressure from changes in the pulsatile component;
   said step of determining a pulsatile component of the acoustic signal comprising:
      determining a difference in phase between the acoustic signal and a reference signal; generating a measurement voltage based of the difference in phase; and
      monitoring the measurement voltage such that the pulsatile component of the acoustic signal can be determined; and said step of determining intracranial pressure from the pulsatile component comprising:
    calibrating a measurement device by inducing a known change in intracranial pressure and measuring the change in the measurement voltage;
    dividing the known change in intracranial pressure by the change in the measurement voltage to obtain a measurement baseline; and
    converting the change in pulsatile component into a change in intracranial pressure with the measurement baseline.

10. The method for non-invasive measurement of changes in intracranial pressure of claim 9 wherein the pulsatile component represents systolic blood pressure partially transferred to the cerebrospinal fluid.

11. The method for non-invasive measurement of changes in intracranial pressure of claim 9 wherein the pulsatile component represents systolic blood pressure partially transferred to the cerebrospinal fluid.

* * * * *